United States Patent [19]

Jones

[11] 4,306,062

[45] Dec. 15, 1981

[54] PROCESS FOR THE PREPARATION OF SUCROSE MONOESTERS

[75] Inventor: Haydn F. Jones, Reading, England

[73] Assignee: Talres Development (N.A.) N.V., Netherlands Antilles

[21] Appl. No.: 153,690

[22] Filed: May 27, 1980

[30] Foreign Application Priority Data

May 24, 1979 [GB] United Kingdom ............... 18082/79

[51] Int. Cl.$^3$ .............................................. C07H 5/02
[52] U.S. Cl. ................................... 536/119; 536/115; 260/410.6
[58] Field of Search ..................... 260/410.6; 536/119, 536/115

[56] References Cited

U.S. PATENT DOCUMENTS

| | | | |
|---|---|---|---|
| 2,893,990 | 7/1959 | Hass | 260/410.6 |
| 2,997,491 | 8/1961 | Huber | 260/410.6 |
| 2,997,493 | 8/1961 | Huber | 260/410.6 |
| 3,378,542 | 4/1968 | O'Boyle | 260/410.6 |

Primary Examiner—John F. Niebling
Attorney, Agent, or Firm—Ostrolenk, Faber, Gerb & Soffen

[57] ABSTRACT

Mono and di-esters of sucrose with long-chain fatty acids are prepared by reacting sucrose with an alkenyl ester of the fatty acid in a polar aprotic solvent under substantially water-free conditions.

15 Claims, No Drawings

PROCESS FOR THE PREPARATION OF SUCROSE MONOESTERS

This invention relates to the preparation of esters of sucrose with long-chain fatty acids, in particular monoesters.

Esters of sucrose with fatty acids, particularly the sucrose monoesters, are well-known to be useful as surfactants, particularly for detergent purposes. They are non-toxic, odourless and tasteless; they are non-irritating to the skin; and, when ingested, they are hydrolysed to form normal food products. They are fully biodegradable under both aerobic and anaerobic conditions, and, unlike most other non-ionic surfactants, they are solid and thus readily usable in powdered products.

British Pat. No. 1,399,053 discloses and claims an important process for the production of surfactant materials containing sucrose mono- and di-esters, in which sucrose is transesterified with a glyceryl triester of a fatty acid under basic catalysts in the absence of a solvent. A process of this type yields a material which contains a mixture of unreacted sucrose, the required sucrose esters, and soap, i.e. the salt of the fatty acid with the alkali metal from the basic catalyst, generally potassium. The product also contains mono- and diglycerides and a small proportion of triglyceride. This mixed product is useful in its own right as a detergent composition or an emulsifier. It can also be purified to produce a higher grade detergent containing less glycerides, or to provide a "sucroglyceride" product containing sucrose, sucrose esters and glycerides in the absence of soap.

Most of the alternatively known transesterification processes also involve reaction of sucrose with a glyceryl or alkyl ester of a fatty acid, but in a solvent. The reaction is usually performed at about 90° C., in the presence of an alkaline catalyst (e.g. potassium carbonate). It is believed necessary to remove all traces of water, by heating the system under reduced pressure as each component is added; and the alcohol released as a by-product of the transesterification must also be removed by prolonged heating of the reaction mixture and reduced pressure, so as to drive the reaction equilibrium in the desired direction.

In a modified form of the solvent transesterification process, sucrose is reacted with an alkyl ester in a solvent such as propylene glycol which dissolves the sucrose but not the fatty component. An emulsifying agent is used, and the reaction is performed in a so-called "micro-emulsion". This process still has to be performed under reduced pressure to drive the equilibrium in the desired direction.

A later modification of the solvent transesterification process described in British Patent Specification No. 1,332,192, uses water as the solvent. The sucrose is completely dissolved in water in the presence of a fatty acid soap, a fatty acid ester and a transesterification catalyst are added, and the mixture is dehydrated under reduced pressure at an elevated temperature so as to produce a homogeneous melt. The melt is then maintained at elevated temperature for the transesterification reaction to take place. This process has several stages, still requires heating under reduced pressure, and the pressure must be carefully controlled in relation to the temperature when producing the dehydrated melt, in order to avoid hydrolysis of the fatty acid ester. The process is, therefore, undesirably complicated for use on an industrial scale.

A solvent-free transesterification process has also been proposed (see J. Amer. Oil Chem. Soc. 1970, 47, (2), 56–60; and U.S. Pat. No. 3,714,144). In this process, the solvent-free transesterification is carried out with sucrose in the molten state; and the process is performed at a temperature of from 170° to 190° C. At this temperature, the molten sucrose is rapidly degraded to a black tarry mass, and thus the reaction with the fatty acid ester must necessarily be performed very quickly. The reaction is generally stopped within twenty minutes, and sometimes after only two minutes. As in the solvent processes, the reaction is performed under reduced pressure, to distil off the alcoholic by-product. Furthermore, the reaction must be performed in the presence of an alkali-free anhydrous soap, which serves to solubilise the fatty acid ester in the molten sucrose and to catalyse the transesterification. Alkoxides, free alkalis and ordinary soaps are entirely unsatisfactory as catalysts in this process, and their presence results in very rapid decomposition of the sucrose and darkening of the reaction mixture. The process thus has disadvantages of its own tending to make it unsatisfactory as a commercial-scale preparation for sucrose ester surfactants. Specifically it is difficult to control, because the reaction must be completed very quickly to avoid degrading the sucrose, it must be performed under reduced pressure, and it requires the use of expensive special catalysts.

None of the above-mentioned processes is particularly selective. For surfactant properties, particularly in the detergent field, it is necessary to have as high a proportion of sucrose monoesters as possible in the product and as low a proportion as possible of higher esters. Some diesters are acceptable, but the nearer the product comes to pure monoester the better.

It has now found that sucrose can be directly reacted with a special class of fatty acid esters to obtain sucrose monoester in high yield, with high conversion of sucrose into ester and virtually negligible soap formation.

The particular class of fatty acid esters used in the process according to the present invention consists of the alkenyl esters, in particular alkenyl esters containing two or three carbon atoms in the alkenyl portion, for example, vinyl and isopropenyl esters.

Unlike other transesterification reactions using fatty acid esters, those involving alkenyl esters are not limited by competition of the alcohol released. The reaction procedes with the fission of the alkenyl ester to provide an acyl radical and a ketone or aldehyde (depending on the alkenyl group). Thus, an equilibrium such as is observed in a conventional transesterification reaction cannot be set up since the aldehyde or ketone takes no further part in the reaction. It may, in any case, be largely removed by distillation. This means that the end product can contain a much higher level of sucrose ester.

The reaction of alkenyl acylates with hydroxy compounds has been known for many years. The general body of literature on this type of reaction is concerned with acid-catalysed reactions. Thus, for example, Hagemeyer and Hull, (Industrial and Engineering Chemistry Vol. 41, No. 12, 2920); Jeffery and Satchell, (J. Chem. Soc. (1962) p. 1876); and Rothman et al., (various publications include Journal of the American Oil Chemists' Society Vol. 45 (1968) p. 189) all describe reactions of vinyl acylates under acid catalysis. Rothman, in fact, claims to have reacted sucrose in these conditions.

However, it has been found that under acid catalysis sucrose is very rapidly hydrolysed to glucose and fructose, and the yield of sucrose esters obtained is negligible.

Other workers, for example Smith and Tuschhoff in U.S. Pat. No. 2,928,828, have used aqueous base-catalysed conditions. The typical conditions involve the use of a considerable excess of alkenyl ester and a relatively high proportion of base, for example over 7% of the total weight of reactants. A completely mixed product containing an average of four ester groups was obtained in a yield (based on sucrose tetraacetate) of about 19%.

It has been found, however, that the Smith and Tuschhoff conditions are not at all suitable for the production of monoesters. With their high base content but only about an equivalent of alkenyl ester, only a trace of sucrose monoester and diester is obtained and, indeed, possibly some breakdown of the sucrose molecule to give glucose and fructose had occurred. With low base content, no sucrose esters were obtained. Thus it would appear that this method is only suitable for the preparation of mixed higher ester, where the forcing conditions of high base level and excess of alkenyl ester apparently contrive to speed the reaction sufficiently.

According to the present invention we have found that in the absence of water and in the presence of no added base catalysts, or only a trace of added base catalyst, it is possible to produce sucrose monoesters in high yield and accompanied by a relatively small proportion of diesters and higher esters. The degree of mono-ester production can be reflected in the esterification number. Thus, pure monoester has an esterification number of 1.0 and pure diester has an esterification number of 2.0. According to the present process, it is possible to obtain a product with an esterification number of less than 1.5. As the amount of base catalyst included in the reaction medium is reduced, we find that the esterification number decreases and products with an esterification number of below 1.3 are possible. Such a product can be obtained with a degree of sucrose conversion of over 70%, leading to a product high in sucrose monoester, low in sucrose and virtually free of soap.

According to the present invention, there is provided a process for the preparation of mono- and di-esters of sucrose and long-chain fatty acids, in which sucrose is reacted with an alkenyl ester of the fatty acid in a polar aprotic solvent in substantially water-free conditions and, optionally, in the presence of an added trace of basic catalyst.

The alkenyl ester of the fatty acid used in the process may be the ester of a fatty acid having at least 8 carbon atoms, preferably at least 12 and most preferably from 16 to 18 carbon atoms in the fatty acid moiety. The ester may be a pure ester of a single fatty acid, or may be the alkenyl ester of a mixture of fatty acids such as that derived from a naturally occurring triglyceride such as tallow, lard, palm oil, cotton seed oil, soy bean oil, olive oil, ground nut oil, coconut oil, castor oil or linseed oil. Stearic acid is preferred and vinyl stearate and isopropenyl stearate may be obtained commercially. Other fatty acid alkenyl esters can be made by methods well-known in the literature, for example by reaction of the fatty acid with an alkyne, or with another alkenyl ester, for example an alkenyl acetate.

The polar aprotic solvent for the reaction according to the present invention should preferably be an amide in which the nitrogen atom is fully substituted. One particularly preferred amide is an N,N-dialkylformamide or N,N-dialkylacetamide, for example dimethylformamide. Another preferred type of amide solvent is an N-alkyl-azacycloalkanone, for example N-methylpyrrolidone.

When a base is added to catalyse the reaction, it is preferably an inorganic base, particularly an alkali metal salt of a weak acid, for example an alkali metal carbonate or bicarbonate. Potassium is the preferred alkali metal. However, the reaction does proceed without any added catalyst, although the reaction rate is considerably slower. In the absence of added catalysts, the esterification number is found to be lowest and this number increases with the amount and strength of the basic catalyst included in the reaction medium. In general, an amount of less than 2% by weight of the total reactants is suitable, preferably less than 1%. When potassium carbonate is used as the added catalyst, an amount of less than 0.7%, preferably less than 0.2%, for example, 0.1 to 0.15%, by weight of the total reactants is advantageous.

The alkenyl ester is used in a ratio of preferably less than 2 moles of ester per mole of sucrose, especially from 0.9 to 1.5 moles per mole of sucrose. A ratio of about 1.2:1.0 is particularly preferred.

The reaction may be effected at a temperature from ambient up to the reflux temperature of the system, preferably from 70° to 90° C., particularly preferably about 80° to 85° C. Under these conditions a reaction time of from 2 to 8 hours is possible and the reaction may be complete even sooner. The reaction time will, in part, depend on the nature of the alkenyl ester. Vinyl esters are considerably more reactive than other esters, such as isopropenyl esters.

The combination of a short reaction time and relatively low temperatures (compared with prior art transesterifications) means that the product obtained contains relatively little degraded sucrose and is of a good colour.

The product can be isolated from the reaction medium quite simply by evaporating the medium to dryness, washing with residue with water and methyl ethyl ketone and evaporating off the methyl ethyl ketone.

The following Examples illustrate the invention:

(a) Materials: Vinyl stearate was supplied by Air Products Ltd., Crewe, Cheshire and manufactured by Air Products and Chemicals Inc., Specialty Gases Dept., Allentown, Pa. 18105 (Commodity No. J82-L-0750).

Isopropenyl stearate was manufactured as the Eastern Regional Research Center of the U.S. Department of Agriculture, Agriculture Research Service, 606E, Mermaid Lane, Philadelphia, Pa. 19118. It was of high purity and showed no signs of impurity when examined by $^1$H.n.m.r. It gave a value of 6.1% soap (as potassium tallowate) by titration. The fatty acid profile (as methyl esters on g.l.c) was myristate, 4.7%, palmitate, 42.3%; palmitoleate, 3.2%; stearate, 42.4%; oleate, 6.6%.

(b) Method: Measured quantities of solutions of dry sucrose in analytical grade solvents were reacted with the alkenyl ester stated, in the presence of the stated amount of catalyst. The reaction were analysed both quantitatively and qualitatively by g.l.c. using direct silylation of the organic solutions.

For comparison, reactions under acid catalysed conditions (in comparative Example A) and under aqueous conditions (in Comparative Examples B–E) were also effected. Comparative Example 3 represents the type of conditions used by Smith and Tuschhoff in U.S. Pat. No. 2,928,828; C represents a modification of B with only a trace of basic catalyst; D represents an aqueous analogue of Example 2; and E represents a further application of the Smith and Tuschhoff conditions but using the same molar equivalent of vinyl acetate as for the vinyl stearate examples.

The results are summarised in the following Tables, in which the following abbreviations are used:

IPS = isopropenyl stearate
VS = vinyl stearate
ME = sucrose monoester
DE = sucrose diester
HE = sucrose higher esters
TSOH = p-toluenesulphonic acid
NA = not analysed (atypical g.l.c. traces)
DMF = N,N-dimethylformamide
NMP = N-methyl pyrrolidone

| Example | 1 | 2 | 3 |
|---|---|---|---|
| Quantity of sucrose (volume; conc.; solvent) | 80ml; 6.25%; DMF | 100ml; 5%; DMF | 100ml; 5%; DMF |
| Alkenyl ester | VS | VS | VS |
| (wt; equivs) | 10.0g; 2.2 | 4.5g; 0.99 | 5.5g; 1.215 |
| Catalyst | $K_2CO_3$ | $K_2CO_3$ | $K_2CO_3$ |
| (wt; % by weight of total reactants) | 100mg; 0.66% | 100mg; 1.04% | 100mg; 0.94% |
| Time (hours) | 2.0 | 2.5 | 6 |
| Temp. (°C.) | 100 | 90 | 83 |
| Products | ME + DE + HE | ME + DE | ME + DE + HE |
| Ratio ME:DE (by moles) | 1:1.39 | 1:0.35 | 1:0.535 |
| Esterification No. | 1.58 | 1.26 | 1.35 |
| Esters in product (% by wt) | — | 79 | 62 |
| Sucrose reacted (% by wt) | — | 81 | 75 |

| Example | 4 | 5 | 6 |
|---|---|---|---|
| Quantity of sucrose (volume; conc.; solvent) | 100ml; 5%; DMF | 100ml; 5%; DMF | 100ml; 5%; DMF |
| Alkenyl ester | VS | VS | VS |
| (wt; equivs) | 5.5g; 1.215 | 5.5g; 1.215 | 5.5g; 1.215 |
| Catalyst | $KHCO_3$ | none | $K_2CO_3$ |
| (wt; % by weight of total reactants) | 100mg; 0.94% | added | 15mg; 0.143% |
| Time (hours) | 8 | 4.5 | 7 |
| Temp. (°C.) | 83 | 80 | 83 |
| Products | ME + DE | ME + DE | ME + DE |
| Ratio ME:DE (by moles) | 1:0.63 | 1:0.23 | 1:0.28 |
| Esterification No. | 1.39 | 1.19 | 1.22 |
| Esters in product (% by wt) | 59 | 22 | 76 |
| Sucrose reacted (% by wt) | 75 | 40 | 74 |

| Example | 7 | 8 | 9 |
|---|---|---|---|
| Quantity of sucrose (volume; conc.; solvent) | 100ml; 5%; DMF | 50ml; 5%; NMP | 50ml; 5%; NMP |
| Alkenyl ester | IPS | IPS | VS |
| (wt; equivs) | 15.6g; 3.3 | 5.0g; 2.1 | 5.0g; 2.2 |
| Catalyst | $K_2CO_3$ | $K_2CO_3$ | $K_2CO_3$ |
| (wt; % by wt of total reactants) | 220mg; 1.06% | 50mg; 0.66% | 50mg; 0.66% |
| Time (hours) | 10 | 2.5 | 2.5 |
| Temp (°C.) | 80 | 80 | 80 |
| Products | ME + DE | ME + DE | ME + DE |
| Ratio ME:DE (by moles) | ~1:0.28 | ~1:0.28 | ~1:0.28 |
| Esterification No. | ~1.22 | ~1.22 | ~1.22 |
| Esters in product (% by wt) | ~40 | ~60 | ~86 |
| Sucrose reacted (% by wt) | 64 | 64 | 94 |

| | Comparative Examples | | |
|---|---|---|---|
| Example | A | B | C |
| Quantity of sucrose (volume; conc.; solvent) | 100ml; 5% DMF | 11.6ml; 43% $H_2O$ | 11.6ml; 43% $H_2O$ |
| Alkenyl ester | IPS | VS | VS |
| (wt; equivs) | | 4.5g; 0.99 | 4.5g; 0.99 |
| Catalyst | TSOH | $Na_2CO_3$ | $K_2CO_3$ |
| (wt; % by wt of total reactants) | 10mg; — | 1.28g; 11.9% | 100mg; 1.04% |
| Time (hours) | 5 | 2 | 2 |
| Temp (°C.) | 80 | 60* | 60* |
| Products | Glucose + | No sucrose | No sucrose |

|  | fructose esters | esters |
|---|---|---|
|  | Comparative Examples | |
| Example | D | E |
| Quantity of sucrose (volume; conc.; solvent) | 100ml; 5% H₂O | 11.6ml; 43% H₂O |
| Alkenyl ester (wt; equivs) | VS 4.5g; 0.99 | VA 1.29g; 0.98 |
| Catalyst (wt; % by weight of total reactants) | $K_2CO_3$ 100mg; 1.04% | $Na_2CO_3$ 1.28g; 16.9% |
| Time (hours) | 2.5 | 2 |
| Temp (°C.) | 90 | 43–45 |
| Products | No sucrose esters | trace sucrose mono- and di-acetates + other products |

*A temperature of 60° was used rather than 43° as in U.S. Pat. Specification No. 2,928,828, in order to melt the vinyl stearate.

I claim:

1. In a process for the preparation of mono- and di-esters of sucrose and a long chain fatty acid by reacting sucrose with an alkenyl ester of the fatty acid, the improvement consisting in that the reaction is effected in a polar aprotic solvent in substantially water-free conditions.

2. A process according to claim 1, in which the reaction is effected in an absence of an acid catalyst.

3. A process according to claim 1, in which the solvent comprises a fully substituted amide.

4. A process according to claim 3, in which the solvent is selected from the group consisting of an N,N-dialkylformamide, an N,N-dialkylacetamide and an N-alkyl-azacycloalkanone.

5. A process according to claim 4, in which the solvent is selected from the group consisting of dimethylformamide and N-methyl pyrrolidone.

6. A process according to claim 1, in which the reaction is effected in the presence of less than 2% by weight of the total reactants of a basic catalyst.

7. A process according to claim 6, in which the catalyst is an alkali metal salt of a weak acid.

8. A process according to claim 7, in which the catalyst is selected from the group consisting of alkali metal carbonates and alkali metal bicarbonates.

9. A process according to claim 8, in which the catalyst is potassium carbonate.

10. A process according to claim 9, in which the carbonate is present at a concentration of less than 0.7% by weight of the total reactants.

11. A process according to claim 10, in which the carbonate is present at a concentration of less than 0.2% by weight of the total reactants.

12. A process according to claim 1, in which the alkenyl ester is used in a ratio of less than 2 moles of ester per mole of sucrose.

13. A process according to claim 12, in which the alkenyl ester is used in a ratio of 0.9 to 1.5 moles per mole of sucrose.

14. A process according to claim 1, effected at a temperature of from 70° to 90° C.

15. A process according to claim 1, in which the alkenyl ester is selected from the group consisting of vinyl and isopropenyl esters.

* * * * *